(12) United States Patent
Hitney et al.

(10) Patent No.: US 8,352,285 B2
(45) Date of Patent: Jan. 8, 2013

(54) DYNAMICALLY ADJUSTING TRIAGE CLASSIFICATION LEVELS

(75) Inventors: Raymond R. Hitney, Buchanan, NY (US); Martin S. Kohn, East Hills, NY (US); Erik T. Mueller, Chevy Chase, MD (US)

(73) Assignee: International Business Machines Corporation, Armonk, NY (US)

( * ) Notice: Subject to any disclaimer, the term of this patent is extended or adjusted under 35 U.S.C. 154(b) by 183 days.

(21) Appl. No.: 12/797,888

(22) Filed: Jun. 10, 2010

(65) Prior Publication Data

US 2011/0307264 A1     Dec. 15, 2011

(51) Int. Cl.
    *G06Q 10/00* (2012.01)
(52) U.S. Cl. .......................................................... 705/2
(58) Field of Classification Search ................... 705/2, 5
    See application file for complete search history.

(56) References Cited

U.S. PATENT DOCUMENTS

| | | | |
|---|---|---|---|
| 5,216,593 A | 6/1993 | Dietrich et al. | |
| 6,230,142 B1 | 5/2001 | Benigno et al. | |
| 6,754,883 B2 | 6/2004 | DeBusk et al. | |
| 7,480,629 B2 | 1/2009 | Dashefsky et al. | |
| 7,493,264 B1 | 2/2009 | Kelly et al. | |
| 7,657,442 B2 | 2/2010 | Merkin | |
| 2002/0077849 A1 | 6/2002 | Baruch et al. | |
| 2002/0082965 A1 | 6/2002 | Loeper | |
| 2003/0028399 A1 | 2/2003 | Davis et al. | |
| 2003/0033180 A1 | 2/2003 | Shekar et al. | |
| 2003/0088441 A1 | 5/2003 | McNerney | |
| 2005/0004828 A1 | 1/2005 | DeSilva et al. | |
| 2006/0100901 A1* | 5/2006 | Glimp et al. | 705/2 |
| 2006/0184412 A1 | 8/2006 | Kagan et al. | |
| 2009/0138300 A1 | 5/2009 | Kagan et al. | |
| 2009/0216747 A1* | 8/2009 | Li et al. | 707/5 |
| 2009/0299928 A1 | 12/2009 | Kongtcheu | |
| 2010/0305966 A1* | 12/2010 | Coulter et al. | 705/2 |

OTHER PUBLICATIONS

G. Stiglic et al., "Intelligent Patient and Nurse Scheduling in Ambulatory Health Care Centers", 2005 27th Annual International Conference of the IEEE Engineering in Medicine and Biology Society, 2006.

(Continued)

*Primary Examiner* — Valerie Lubin
(74) *Attorney, Agent, or Firm* — John R. Pivnichny; Law Office of Jim Boice

(57) ABSTRACT

An initial triage level classification for a latest patient to arrive at an emergency department (ED) is received. Availability levels of resources needed to treat the latest patient are electronically collected, along with triage level classifications for all other patients currently in the ED. The initial triage level classification of the latest patient is adjusted upward or downward based on the availability levels of resources needed to treat the latest patient and based on the triage level classifications for the patients in the ED. The triage level classifications for all patients currently in the ED are summed up. If a sum of all triage level classifications exceeds a first predetermined threshold, other resources are reallocated in order to provide the resources needed to treat the latest patient to arrive at the ED. If the sum of all triage level classifications exceeds a second predetermined threshold, then a disaster plan is implemented.

6 Claims, 4 Drawing Sheets

OTHER PUBLICATIONS

A. Tay, "Assessing Competition in Hospital Care Markets: The Importance of Accounting for Quality Differentiation", Rand Journal of Economics, vol. 34, No. 4, pp. 786-814, Winter 2003.

JMH Vissers, "Patient Flow-Based Allocation of Inpatient Resources: A Case Study", European Journal of Operational Research, vol. 105, No. 2, pp. 356-370, Mar. 1, 1998.

MD Rossetti et al., "Emergency Department Simulation and Determination of Optimal Attending Physician Staffing Schedules", Proceedings of the 1999 Winter Simulation Conference, pp. 1532-1540, 1999.

C. Jurishica, "Emergency Department Simulations: Medicine for Building Effective Models", Proceedings of the 2005 Winter Simulation Conference, pp. 2674-2680, 2005.

A. Wiinamaki et al., "Using Simulation in the Architectural Concept Phase of an Emergency Department Design", Proceedings of the 2003 Winter Simulation Conference, pp. 1912-1916, 2003.

H. Xie et al., "A Semi-Open Queueing Network Approach to the Analysis of Patient Flow in Healthcare Systems", 20th IEEE International Symposium on Computer-Based Medical Systems, pp. 719-724, IEEE Computer Society, Los Alamitos, CA, USA, Jun. 2007.

\* cited by examiner

DYNAMICALLY ADJUSTING TRIAGE CLASSIFICATION LEVELS

BACKGROUND

The present disclosure relates to the field of computers, and specifically to the use of computers with patient triage classifications. Still more particularly, the present disclosure relates to the use of computers to dynamically adjust triage classification levels.

BRIEF SUMMARY

A computer implemented method, system and/or computer program product enable an emergency department (ED) to dynamically adjust to changing triage conditions. An initial triage level classification for a latest patient to arrive at the ED is received. Availability levels of resources needed to treat the latest patient are electronically collected, along with triage level classifications for all other patients currently in the ED. The initial triage level classification of the latest patient is adjusted upward or downward based on the availability levels of resources needed to treat the latest patient and based on the triage level classifications for the patients in the ED. The triage level classifications for all patients currently in the ED are summed. If a sum of all triage level classifications exceeds a first predetermined threshold, other resources are reallocated in order to provide the resources needed to treat the latest patient to arrive at the ED. If the sum of all triage level classifications exceeds a second predetermined threshold, then a disaster plan is implemented.

DETAILED DESCRIPTION

Figure 1:
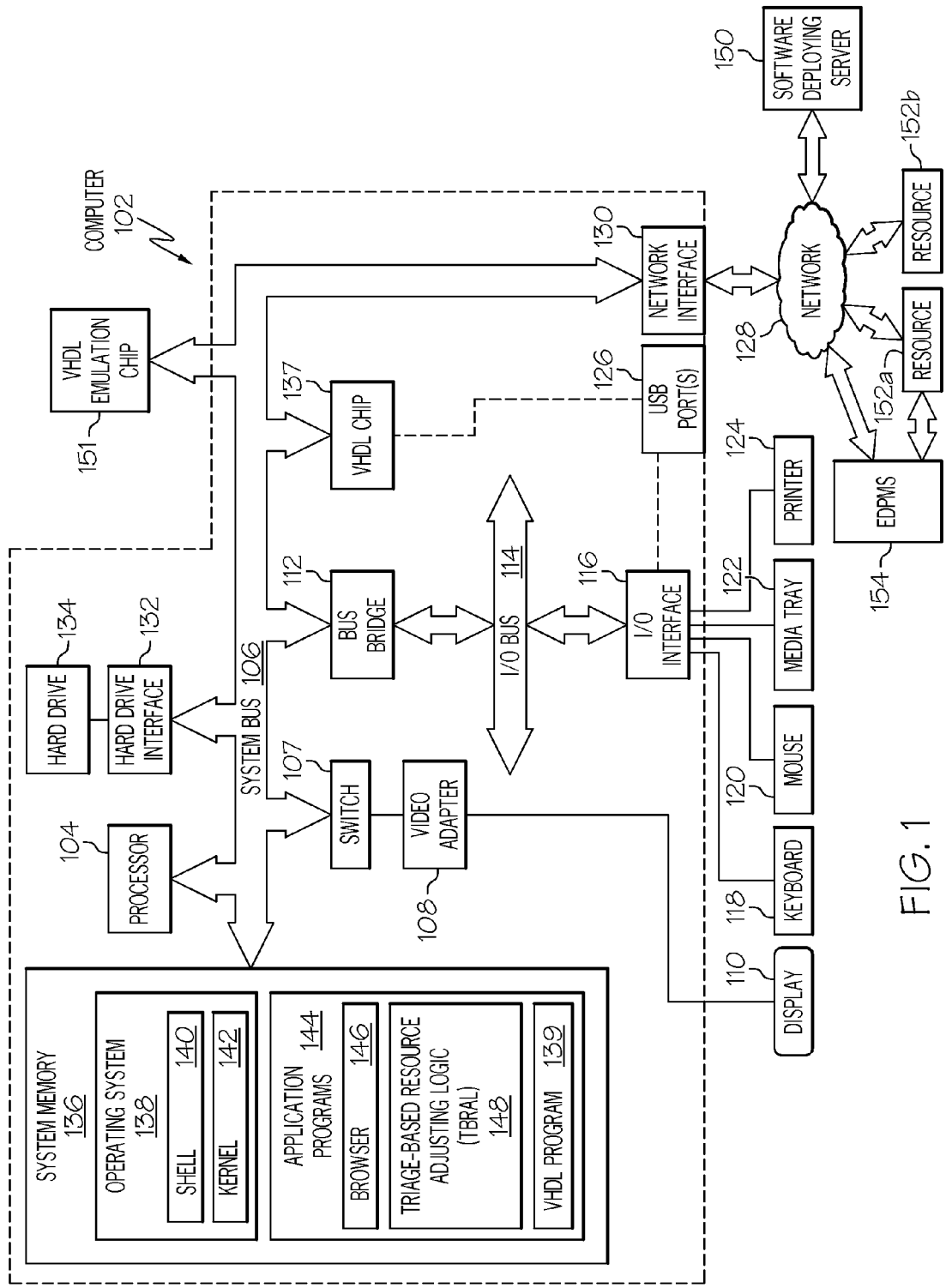
FIG. 1 depicts an exemplary computer in which the present disclosure may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, resources 152a-b, and/or emergency department patient monitoring system (EDPMS) 154.

Computer 102 includes a processor 104 that is coupled to a system bus 106. Processor 104 may utilize one or more processors, each of which has one or more processor cores. A video adapter 108, which drives/supports a display 110, is also coupled to system bus 106. In one embodiment, a switch 107 couples the video adapter 108 to the system bus 106. Alternatively, the switch 107 may couple the video adapter 108 to the display 110. In either embodiment, the switch 107 is a switch, which may be mechanical, that allows the display 110 to be coupled to the system bus 106, and thus to be functional only upon execution of instructions (e.g., triage-based resource adjusting logic—TBRAL 148 described below) that support the processes described herein.

System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and (if a VHDL chip 137 is not utilized in a manner described below), external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other described computer systems.

Application programs 144 in computer 102's system memory (as well as software deploying server 150's system memory) also include a triage-based resource adjusting logic (TBRAL) 148. TBRAL 148 includes code for implementing the processes described herein, including those described in FIGS. 2-4. In one embodiment, computer 102 is able to download TBRAL 148 from software deploying server 150, including in an on-demand basis, wherein the code in TBRAL 148 is not downloaded until needed for execution to define and/or implement the improved enterprise architecture described herein. Note further that, in one embodiment of the present invention, software deploying server 150 performs all of the functions associated with the present invention (including execution of TBRAL 148), thus freeing computer 102 from having to use its own internal computing resources to execute TBRAL 148.

Also stored in system memory 136 is a VHDL (VHSIC hardware description language) program 139. VHDL is an exemplary design-entry language for field programmable gate arrays (FPGAs), application specific integrated circuits (ASICs), and other similar electronic devices. In one embodiment, execution of instructions from TBRAL 148 causes VHDL program 139 to configure VHDL chip 137, which may be an FPGA, ASIC, etc.

In another embodiment of the present invention, execution of instructions from TBRAL 148 results in a utilization of VHDL program 139 to program a VHDL emulation chip 151. VHDL emulation chip 151 may incorporate a similar architecture as described above for VHDL chip 137. Once TBRAL 148 and VHDL program 139 program VHDL emulation chip 151, VHDL emulation chip 151 performs, as hardware, some or all functions described by one or more executions of some or all of the instructions found in TBRAL 148. That is, the VHDL emulation chip 151 is a hardware emulation of some or all of the software instructions found in TBRAL 148. In one embodiment, VHDL emulation chip 151 is a programmable read only memory (PROM) that, once burned in accordance with instructions from TBRAL 148 and VHDL program 139, is permanently transformed into a new circuitry that performs the functions needed to perform the process described below in FIGS. 2-4.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
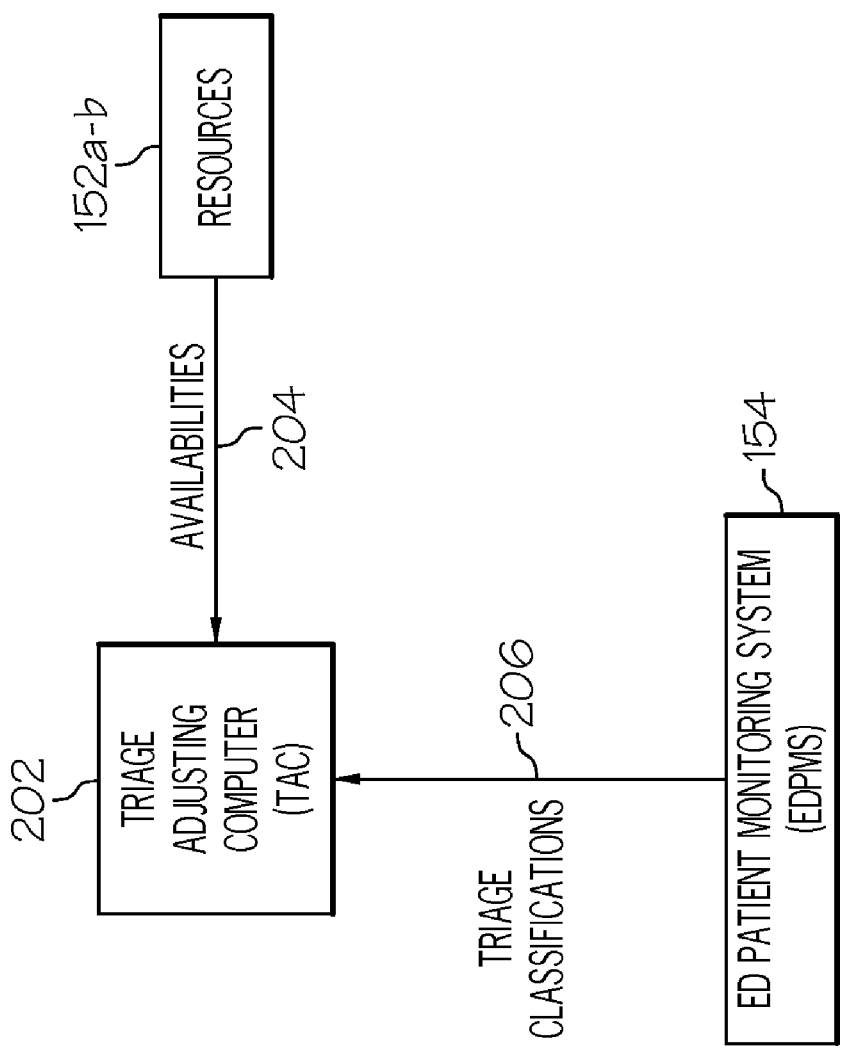
FIG. 2 illustrates relationships among a triage adjusting computer (TAC), resources, and an emergency department patient monitoring system (EDPMS)
Figure 3:
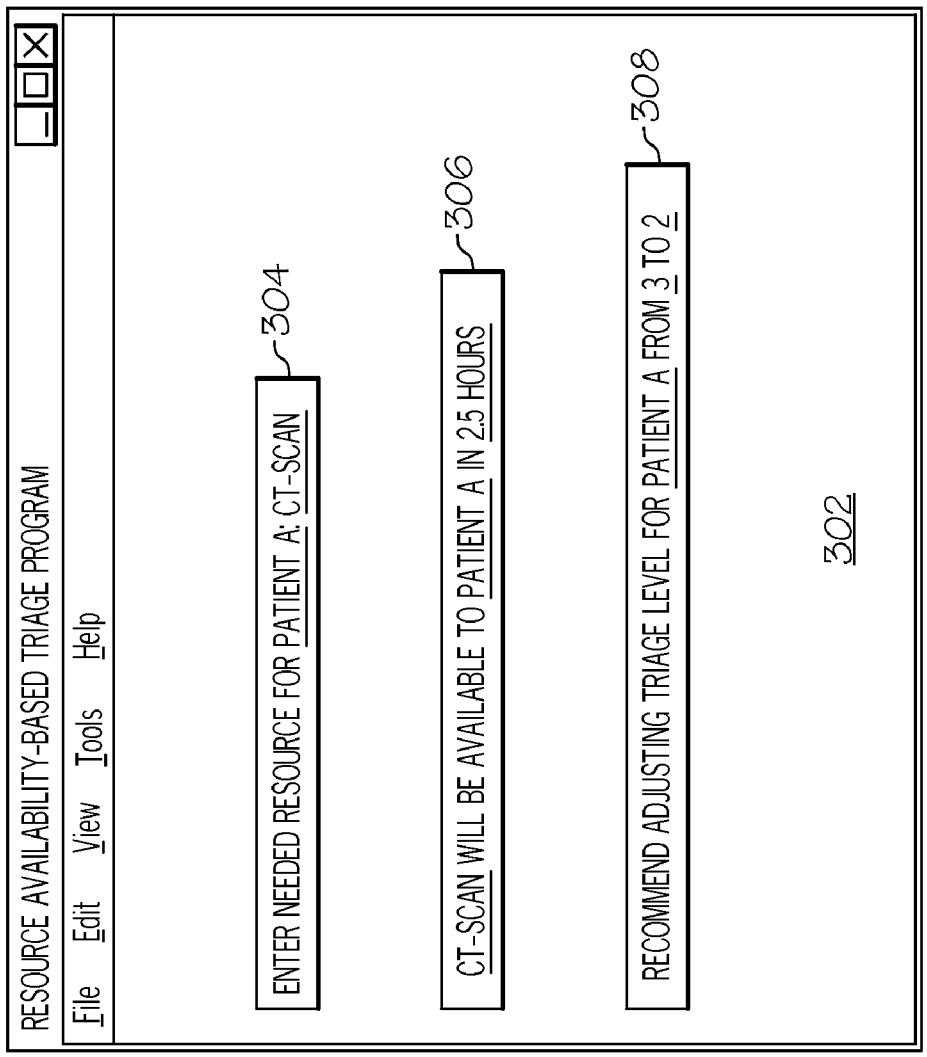
FIG. 3 depicts an exemplary user interface (UI) used to request a resource for a patient in an emergency department (ED)

Referring now to FIG. 2, a triage adjusting computer (TAC) 202, which is analogous to computer 102 shown in FIG. 1, is coupled to resources 152*a-b* (where "b" is an integer) and an emergency department patient monitoring system (EDPMS) 154, also shown in FIG. 1. Resources 152*a-b* may be any resource needed by a patient in an emergency department (ED), also called an emergency room (ER). The ED/ER is a department of a hospital in which emergency patients arrive via ambulance, personal vehicles, or by walking in order to receive emergency medical treatment for acute medical maladies or conditions. Resources 152*a-b* include, but are not limited to, an open bed in the ED, an open bed outside the ED but within the same or a different hospital, radiology equipment, radiology technicians, medical laboratory equipment, medical laboratory technicians, nurses, and physicians. Part of resources 152*a-b* is logic and transmission means (e.g., processor 104, TBRAL 148 and network interface 130 shown in FIG. 1 as exemplary components of resources 152*a-b*) for communicating the availability level (availabilities 204) of these resources. For example, if the resource is hardware such as a computer tomography (CT) machine, logic (e.g., computer 102) associated with that CT machine is able to communicate to TAC 202 how much longer the CT machine will be in use (if being currently used), what technicians are operating the machine and when they are scheduled to go off duty, what technicians, if any, are on stand-by to be called in if needed, etc. All of the information is conveyed in messages depicted as availabilities 204. If a resource is purely a health care provider, such as a nurse or doctor, then logic (e.g., computer 102) associated with that personnel resource may be a scheduling computer, an automated caller to call an off-duty worker in from her home or another department, a tracking system to identify where the needed worker is currently located (in real time) within the hospital, etc.

EDPMS 154 is a tracking system that monitors patients within the emergency department (ED) in real time. EDPMS 154 is also aware of, and in one embodiment is used to calculate, the triage classifications 206 for each patient within the ED. While EDPMS 154 can utilize any triage system, in one embodiment EDPMS 154 utilizes the Emergency Severity Index (ESI) system. Under the ESI system, Level 1 patients are those that require immediate life-saving intervention. Level 2 patients are those that are at high risk, or are confused and disoriented, or are in severe pain. Typically, Level 2 patients should be seen within 30 minutes. Levels 3-5 are for patients who do not require immediate attention. Level 5 patients require no services/resources outside of the ED (i.e., they do not require any lab work, x-rays, etc.). Level 4 patients require one service/resource outside of the ED. Level 3 patients require multiple services/resources outside of the ED. Note that a Level 3 patient can be moved up to Level 2 if vital signs (heart rate, blood pressure, oxygen saturation) go into a danger zone, even if the patients do not meet the usual requirements to be classified as a Level 2 patient.

In a manner described in detail herein, TAC 202 utilizes availabilities 204 or resources 152*a-b* and triage classifications 206 of other patients in the ED as inputs to adjust the triage level of each new patient to the ED. In order to obtain availability information from and about one or more of the resources 152*a-b*, a health care provider in the ED can utilize a user interface (UI) such as UI 302 shown in FIG. 3. Assume that the newest patient to come into the ED ("Patient A") is initially classified at Level 3 in the ESI system. As depicted in block 304, the user has entered that newly-arrived "Patient A" in the ED needs a CT scan. The appropriate resource 152 responds with a message (availabilities 204 shown in FIG. 2) that the CT machine will not be available for 2.5 hours, as presented in block 306. TAC 202 therefore recommends that the triage level for "Patient A" be moved up from Level 3 to Level 2, as presented in block 308. By moving "Patient A" up to Level 2, she will be placed ahead of other Level 3 patients. Thus, the currently described process creates a triage system that does not just look at the patient's condition in a stand-alone manner, but also considers the conditions of other patients and the availability of resources to fine-tune the first patient's triage level.

Figure 4:
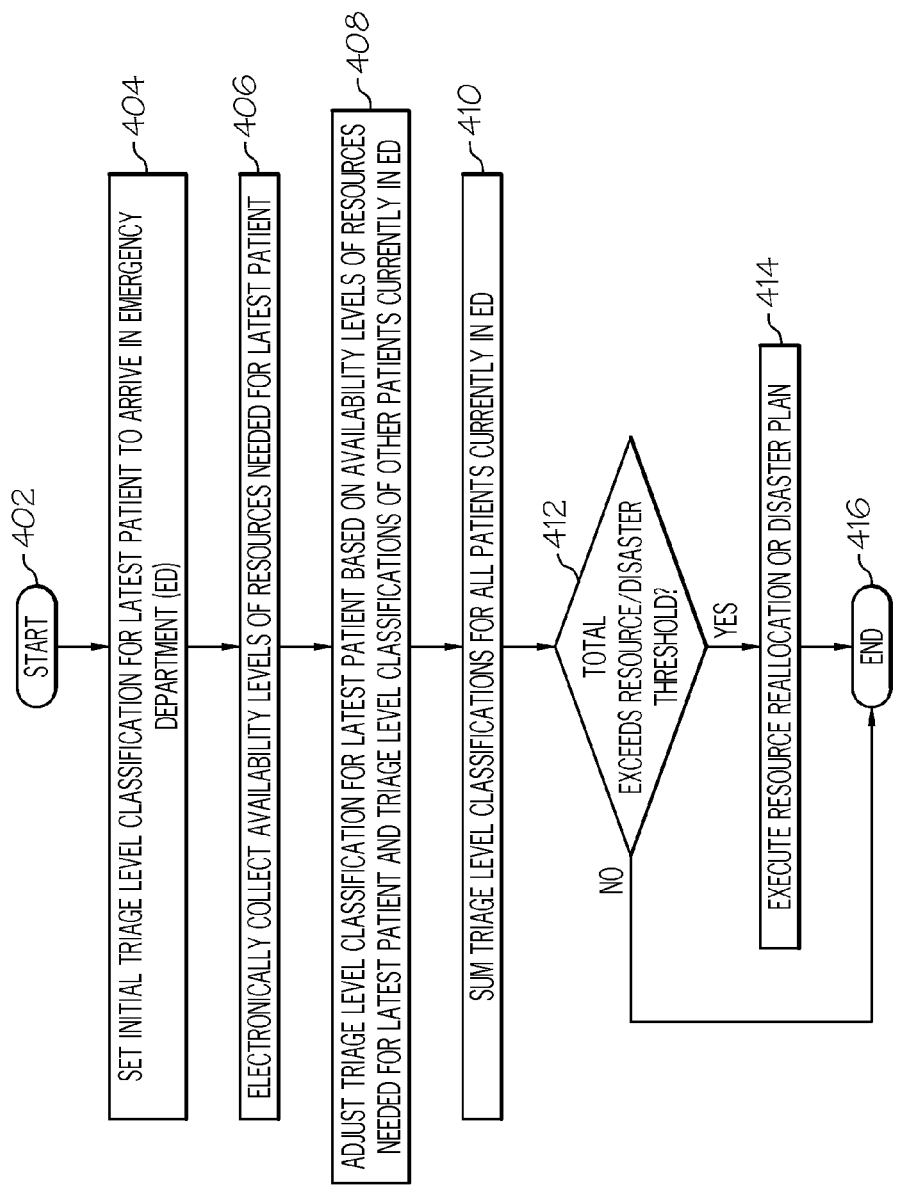
FIG. 4 is a high level flow chart of one or more exemplary steps taken by a processor to enable an ED to dynamically adjust to changing triage conditions.

With reference now to FIG. 4, a high level flow chart of one or more steps executed by a computer/processor for dynamically adjusting to changing triage conditions in an emergency department is presented. After initiator block 402, a processor receives an initial triage level classification for a latest patient to arrive at an emergency department (block 404). As described above in exemplary form in FIGS. 2-3, availability levels of resources needed to treat the latest patient to arrive at the emergency department are electronically collected (block 406). The computer/processor (i.e., TAC 202 shown in FIG. 2) receives triage level classifications for all other patients currently in the emergency department, and then adjusts the initial triage level classification of the latest patient based on the availability levels of resources needed to treat the latest patient and based on the triage level classifications for said all other patients currently in the emergency department (block 408).

As depicted in block 410, all triage level classifications for all patients currently in the emergency department are then summed up. A query (query block 412) is made to determine if the summed-up triage levels exceed a first or second predetermined level. If the sum of all triage level classifications exceeds a first predetermined threshold, the processor/computer issues messages to reallocate other resources in order to provide the resources needed to treat the latest patient to arrive at the emergency department. Similarly, if the sum of all triage level classifications exceeds a second predetermined threshold that is greater than the first predetermined threshold, the processor/computer automatically implements a disaster plan to prevent additional patients from arriving at the emergency department (block 414). In one embodiment, the disaster plan is based on a prediction of how long the ED will be unable to accept new patients. For example, the processor/computer can calculate, based on historical data, a predicted length of down time during which resources will not be adequate to permit receiving new patients at the emergency department. Based on this calculation, the processor/computer automatically executes the disaster plan by instructing local broadcasting media to broadcast a message to the general public that the emergency department is unable to receive new patients for the predicted length of down time. The process ends at terminator block 416.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer implemented method of dynamically adjusting to changing triage conditions in an emergency department, the computer implemented method comprising:
a processor receiving an initial numerical triage level classification for a latest patient to arrive at an emergency department;
electronically collecting availability levels of resources needed to treat the latest patient to arrive at the emergency department;
the processor receiving numerical triage level classifications for all other patients currently in the emergency department;
the processor adjusting the initial numerical triage level classification of the latest patient based on the availability levels of resources needed to treat the latest patient and based on the numerical triage level classifications for said all other patients currently in the emergency department;
the processor summing all numerical triage level classifications for all patients currently in the emergency department;
in response to a sum of all numerical triage level classifications exceeding a first predetermined threshold, the processor issuing messages to reallocate other resources in order to provide the resources needed to treat the latest patient to arrive at the emergency department;
in response to the sum of all numerical triage level classifications exceeding a second predetermined threshold that is greater than the first predetermined threshold, the processor automatically implementing a disaster plan to prevent additional patients from arriving at the emergency department;
the processor calculating, based on historical data, a predicted length of down time during which resources will not be adequate to permit receiving new patients at the emergency department; and
the processor executing the disaster plan by instructing local broadcasting media to broadcast a message to the general public that the emergency department is unable to receive new patients for the predicted length of down time.

2. The computer implemented method of claim 1, wherein the resources needed to treat the latest patient comprise an open bed in the emergency department, radiology equipment, radiology technicians, medical laboratory equipment, medical laboratory technicians, nurses, and physicians, and wherein reallocating the radiology technicians, laboratory technicians, nurses and physicians comprises calling off-duty personnel in to work and relocating personnel from other departments.

3. A computer program product for dynamically adjusting to changing triage conditions in an emergency department, the computer program product comprising:
a computer readable storage medium;
first program instructions to receive an initial numerical triage level classification for a latest patient to arrive at an emergency department;
second program instructions to electronically collect availability levels of resources needed to treat the latest patient to arrive at the emergency department;
third program instructions to receive numerical triage level classifications for all other patients currently in the emergency department;
fourth program instructions to adjust the initial numerical triage level classification of the latest patient based on the availability levels of resources needed to treat the latest patient and based on the numerical triage level classifications for said all other patients currently in the emergency department;
fifth program instructions to sum all numerical triage level classifications for all patients currently in the emergency department;
sixth program instructions to, in response to a sum of all numerical triage level classifications exceeding a first predetermined threshold, issue messages to reallocate other resources in order to provide the resources needed to treat the latest patient to arrive at the emergency department; and
seventh program instructions to, in response to the sum of all numerical triage level classifications exceeding a second predetermined threshold that is greater than the first predetermined threshold, automatically implement a disaster plan to prevent additional patients from arriving at the emergency department;

eighth program instructions to calculate, based on historical data, a predicted length of down time during which resources will not be adequate to permit receiving new patients at the emergency department;

ninth program instructions to execute the disaster plan by instructing local broadcasting media to broadcast a message to the general public that the emergency department is unable to receive new patients for the predicted length of down time; and wherein the first, second, third, fourth, fifth, sixth, seventh, eighth, and ninth program instructions are stored on the computer readable storage medium.

4. The computer program product of claim 3, wherein the resources needed to treat the latest patient comprise an open bed in the emergency department, radiology equipment, radiology technicians, medical laboratory equipment, medical laboratory technicians, nurses, and physicians, and wherein reallocating the radiology technicians, laboratory technicians, nurses and physicians comprises calling off-duty personnel in to work and relocating personnel from other departments.

5. A computer system comprising:

a central processing unit (CPU), a computer readable memory, and a computer readable storage medium;

first program instructions to receive an initial numerical triage level classification for a latest patient to arrive at an emergency department;

second program instructions to electronically collect availability levels of resources needed to treat the latest patient to arrive at the emergency department;

third program instructions to receive numerical triage level classifications for all other patients currently in the emergency department;

fourth program instructions to adjust the initial numerical triage level classification of the latest patient based on the availability levels of resources needed to treat the latest patient and based on the numerical triage level classifications for said all other patients currently in the emergency department;

fifth program instructions to sum all numerical triage level classifications for all patients currently in the emergency department;

sixth program instructions to, in response to a sum of all numerical triage level classifications exceeding a first predetermined threshold, issue messages to reallocate other resources in order to provide the resources needed to treat the latest patient to arrive at the emergency department; and seventh program instructions to, in response to the sum of all numerical triage level classifications exceeding a second predetermined threshold that is greater than the first predetermined threshold, automatically implement a disaster plan to prevent additional patients from arriving at the emergency department;

eighth program instructions to calculate, based on historical data, a predicted length of down time during which resources will not be adequate to permit receiving new patients at the emergency department;

ninth program instructions to execute the disaster plan by instructing local broadcasting media to broadcast a message to the general public that the emergency department is unable to receive new patients for the predicted length of down time; and wherein the first, second, third, fourth, fifth, sixth, seventh, eighth, and ninth program instructions are stored on the computer readable storage medium for execution by the processor via the computer readable memory.

6. The computer system of claim 5, wherein the resources needed to treat the latest patient comprise an open bed in the emergency department, radiology equipment, radiology technicians, medical laboratory equipment, medical laboratory technicians, nurses, and physicians, and wherein reallocating the radiology technicians, laboratory technicians, nurses and physicians comprises calling off-duty personnel in to work and relocating personnel from other departments.

* * * * *